(12) United States Patent
Lee et al.

(10) Patent No.: US 8,101,355 B2
(45) Date of Patent: Jan. 24, 2012

(54) METHOD FOR CLONING AND EXPRESSING TARGET GENE BY HOMOLOGOUS RECOMBINATION

(75) Inventors: Seung-Goo Lee, Daejeon (KR); Jae-Jun Song, Daejeon (KR); Jeong-Min Lee, Daegu-si (KR); Jae-Seok Ha, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 206 days.

(21) Appl. No.: 12/559,345

(22) Filed: Sep. 14, 2009

(65) Prior Publication Data

US 2010/0009450 A1    Jan. 14, 2010

Related U.S. Application Data

(63) Continuation of application No. 11/487,106, filed on Jul. 14, 2006, now abandoned.

(30) Foreign Application Priority Data

Dec. 2, 2005    (KR) ........................ 10-2005-0116672

(51) Int. Cl.
*C12Q 1/68* (2006.01)
(52) U.S. Cl. ........................................ 435/6.1; 435/6.15
(58) Field of Classification Search ........................ None
See application file for complete search history.

(56) References Cited

U.S. PATENT DOCUMENTS

2007/0148775 A1    6/2007    Lee et al.

FOREIGN PATENT DOCUMENTS

WO    9929837 A2    6/1999

OTHER PUBLICATIONS

Datsenko, Kirill A., et al., "One-step inactivation of chromosomal genes in *Escherichia coli* K-12 using PCR products", "Proc. Natl. Acad. Sci. USA", Jun. 6, 2000, pp. 6640-6645, vol. 97, No. 12.
Zhang, Youming, et al., "A new logic for DNA engineering using recombination in *Escherichia coli*", "Nature Genetics", Oct. 1998, pp. 123-128, vol. 20, No. 2.
Zhang, Youming, et al., "DNA cloning by homologous recombination in *Escherichia coli*", "Nature Biotechnology", Dec. 2000, pp. 1314-1317, vol. 18, No. 12.

*Primary Examiner* — Michele K Joike
(74) *Attorney, Agent, or Firm* — Kelly K. Reynolds; Steven J. Hultquist; Hultquist IP

(57) ABSTRACT

A method for cloning and expressing a target gene by homologous recombination, and more particularly a method for cloning and expressing a target gene by homologous recombination, wherein a host cell transformed with a recombinant vector and a plasmid containing a recombinase system is introduced with a linear DNA fragment comprising a target gene and a sequence having homology to the recombinant vector. Because complicated genetic engineering steps, such as the restriction enzyme treatment and ligation of a vector and a target gene, are not required, the cloning of a gene can be performed without needing a high degree of skill, and enzyme cost can be reduced. The inventive method can be effectively used for the massive, high-speed cloning and protein expression of genes, and the disclosed pRMT-iTGR system can be used as an analytical means for improving high-efficiency recombinase.

4 Claims, 5 Drawing Sheets

FIG. 2

```
T7 promoter              lac operator         Xba I                        RBS(I)
TAATACGACTCACTATAGGGGAATTGTGAGCGGATAACAATTCCCGTCTAGAAATAATTTTGTTTAACTTTAAGAAGGAGATATACATCCA
                                                      Homologous sequence
                                                    Structural gene of cat without start codon
TGGATCTTAGTATATTAGTTAAGTATAAGATATACATGAGAAAAAAATCACTGGATATACCACCGTTGATATATCCCAATGGCATCGTAAA
                                            Homologous sequence
GAACATTTTGAGGCATTTCAGTCAGTTGCTCAATGTACCTATAACCAGACCGTTCAGCTGGATATTACGGCCTTTTTAAAGACCGTAAAGA AAAATAAGCACAAGTTTTATCCGGCCTTTATTCACATTCTTGCCCGCCTGATGAATGCTCATCCGGAATTCCGTATGGCAATGAAAGACGG TGAGCTGGTGATATGGGATAGTGTTCACCCTTGTTACACCGTTTTGCATGAGCAAACTGAAACGTTTTCATCGCTCTGGAGTGAATACCAC GACGATTTCCGGCAGTTTCTACACATATATTCGCAAGATGTGGCGTGTTACGGTGAAAACCTGGCCTATTTCCCTAAAGGGTTTATTGAGA ATATGTTTTCGTCTCAGCCAATCCGTGGGTGAGTTTCACCAGTTTTGATTTAAACGTGGCCAATATGGACAAGTTCTTCGCCCCCGTTTT CACCATGGGCAAATATTATACGCAAGGCGACAAGGTGCTGATGCCGCTGGCGATTCAGGTTCATCATGCCGTTTGTGATGGCTTCCATGTC

GGCAGAATGCTTAATGAATTACAACAGTACTGCGATGAGTGGCAGGGCGGGGCGTAA    (SEQ ID NO: 8)
```

FIG. 3

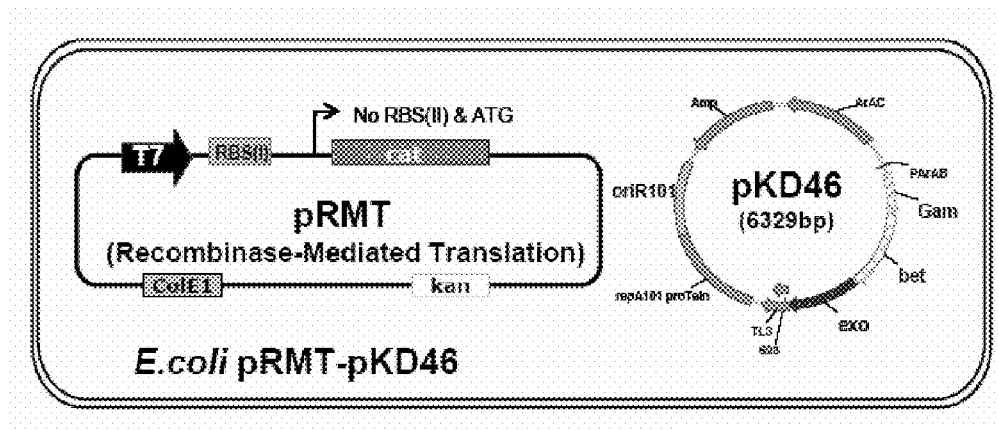

METHOD FOR CLONING AND EXPRESSING TARGET GENE BY HOMOLOGOUS RECOMBINATION

CROSS-REFERENCE TO RELATED APPLICATION

This application is a continuation application of U.S. patent application Ser. No. 11/487,106, which claims priority under 35 USC 119 to Korean Patent Application No. 10-2005-116672 filed Dec. 2, 2005. The disclosures of the foregoing applications are hereby incorporated by reference in their entireties.

BACKGROUND OF THE INVENTION

1. Field of the Invention

The present invention relates to a method for cloning and expressing a target gene by homologous recombination, and more particularly to a method for cloning and expressing a target gene by homologous recombination, wherein a host cell transformed with a recombinant vector and a plasmid containing a recombinase system is introduced with a linear DNA fragment which contains a target gene and a sequence having homology to the recombinant vector.

2. Background of the Related Art

DNA cloning refers to a technique for making a large amount of same gene family by linking a target gene to a self-replicable vector, such as plasmid, phage or cosmid, and introducing the vector into a host such as E. coli to proliferate the target gene. Cloning and sub-cloning in E. coli is performed through a method comprising linking a target gene amplified by a technique such as polymerase chain reaction (PCR) to a vector having a replication origin and an antibiotic selection marker using DNA ligase, introducing the resulting vector into E. coli cells, examining the antibiotic resistance of the bacteria and selecting the cloned cells.

This general cloning technique forms the basis of modern bioengineering and is widely used in the cloning and high-speed protein expression of mass amount of genes based on genetic information which has explosively increased after the human genome project accomplished. However, in the prior genetic engineering technique, there are limitations in that inserted DNA and a vector should be cut with a restriction enzyme at the same recognition site, and the restriction enzyme should be selected from those which do not cut the inside of the insertion DNA or vector. Also, the process of treating the inserted DNA and the vector with the restriction enzyme and ligase requires a skill, and much cost is incurred due to expensive enzymes.

Since the year 1990, interest in a genetic engineering technique utilizing sequence-specific recombinase, which recognizes a specific base sequence to promote the recombination between DNA fragments, has increased. Particularly, a Gateway system (Invitrogen Co.) for cloning genes using integrase that recognizes specific DNA sequences, such as attL, attR, attB and attP, has been developed and widely used in the rapid cloning and protein expression of mass amount of genes. This technique is performed by in vitro genetic engineering in the same manner as the conventional restriction enzyme-ligation reaction, but is a novel cloning method that utilizes LR clonase linking linear DNA fragments with attL or attR, and BP clonase mediating the recombination between attP and attB. In this method, a target gene can be cloned into an entry vector by conventional genetic engineering, and then transferred into various expression vectors by homologous recombination. Thus, this method is highly advantageous for the rapid sub-cloning and expression verification of mass amount of genes.

Meanwhile, if DNA fragments showing sequences identical at more than several hundreds of bases are present in E. coli cells, homologous recombination can occur due to recA and recBCD of E. coli itself. However, if homologous DNAs are less than 40-50 bases in length, genetic recombination by E. coli itself will not occur, and only if phage-derived recombinase Redα/β or RecE/T system is introduced, the recombination between homologous genes will occur. This genetic recombination utilizing short-length homologous DNA fragments can be used in a technique for manipulating microbial genomes, or in vivo cloning which is not affected by restriction enzymes/ligases (Zhang et al., Nature Genetics, 20:123, 1998, Zhang et al., Nature Biotechnology, 18:1314, 2000).

To perform in vivo cloning by the homologous recombination between a linearized plasmid vector and a PCR product, a method was used wherein homologous DNA of 40-50 bases in length is placed at both ends of inserted DNA, a vector is treated with restriction enzyme such that the homologous DNA region are also placed at both ends of the vector, and the vector is introduced into E. coli containing homologous recombinase. In this case, because the linearized cloning vector loses the replication ability of a circular plasmid, and thus does not show antibiotic resistance, the use of antibiotic resistance allows the determination of whether in vivo cloning is successful or not. Although this method is characterized by using recombinase in vivo in place of restriction enzymes or ligases, it has a shortcoming in that the linearized vector consisting of homologous DNA should also be constructed and used.

Proteomics, protein chips, structural biology and the like, which have recently been rapidly advanced, show a need for a genetic engineering technique that can easily clone mass amount of genes and rapidly express a target protein. Particularly, because it is very difficult to perform the existing cloning technique requiring a high degree of skill in an automatic and high-speed manner, there is a need for the development of an easy and rapid gene cloning and protein expression technique.

The present inventors have conducted studies to solve the above-described problems and, as a result, found that, if a target gene fragment is prepared to include sequences having homology to the forward ribosome recognition site and a portion of the region downstream of the promoter of a recombinant vector and to the backward ribosome recognition sequence and start codon of a first selection marker gene and is introduced into a host cell transformed with a plasmid, containing a recombinase system, and the recombinant vector, containing the first selection marker gene having deletions of the ribosome recognition sequence and the start codon, easy cloning of a target gene and the high-speed expression of protein can be achieved by homologous recombination without needing complicated genetic engineering steps, such as the restriction enzyme treatment and ligation of the vector and the inserted fragment, thereby completing the present invention.

SUMMARY OF THE INVENTION

It is an object of the present invention to provide a method for cloning and expressing a target gene by homologous recombination, which can easily clone the target gene and express a protein at high speed, without needing complicated genetic engineering steps, such as the restriction enzyme digestion of a vector, and the ligation of an inserted fragment.

To achieve the above object, the present invention provides a method for cloning and expressing a target gene by homologous recombination, the method comprising the steps of:

(a) preparing a recombinant vector containing (i) a first selection marker gene having deletions of a backward ribosome recognition sequence and a start codon, and thus having no expression ability, (ii) a second selection marker gene that can be expressed, (iii) a promoter and (iv) a forward ribosome recognition sequence, which is constructed such that, if a iTGR (insert for Target Gene and RBS) fragment is inserted between the forward ribosome recognition sequence and the first selection marker gene, the target gene and the first selection marker gene will be expressed;

(b) preparing a microorganism for homologous recombination by introducing the recombinant vector into a microorganism including a plasmid containing a homologous recombination-promoting gene, and thereby;

(c) introducing a linear DNA fragment into the microorganism for homologous recombination, the linear DNA fragment comprising:
 (i) a base sequence of a target gene,
 (ii) a base sequence located at the 5'-terminus of the target gene, which has a forward ribosome recognition sequence of the recombinant vector prepared in the step (a) and a homologous sequence to a portion of the region downstream of the promoter,
 (iii) a base sequence located at the 3'-terminus of the target gene, which has the backward ribosome recognition sequence of the first selection marker gene of the recombinant vector prepared in the step (a), start codon and a homologous sequence to 5'-terminus of the first selection marker gene; and (d) selecting a transformed microorganism introduced with the target gene using the first selection marker gene and the second selection marker gene.

In the inventive method, the iTGR fragment may comprise the target gene, and the backward ribosome recognition sequence and translational start codon of the first selection marker gene.

In the inventive method, the promoter is preferably T7 promoter, and the first selection marker gene is preferably a chloramphenicol-resistant gene (cat). Also, the homologous recombination-promoting gene is preferably a Redα/β or RecE/T gene.

In the inventive method, the step (d) preferably comprises selecting a microorganism expressing the first selection marker gene as the microorganism introduced with the target gene. Also, the selection step (d) preferably comprises selecting a microorganism growing in the presence of the first selection marker as the microorganism introduced with the target gene.

In another aspect, the present invention provides a recombinant vector which contains a first selection marker gene having deletions of a ribosome recognition sequence and a start codon, and thus having no expression ability, a second selection marker gene that can be expressed, a promoter and a forward ribosome recognition sequence, and which is constructed such that, if a iTGR fragment is inserted between the forward ribosome recognition sequence and the first selection marker gene, the iTGR fragment and the first selection marker gene will be expressed.

In the inventive recombinant vector, the iTGR fragment may comprise a target gene and the backward ribosome recognition sequence and start codon of the first selection marker gene.

In the inventive recombinant vector, the promoter is preferably T7 promoter, and the first selection marker gene is preferably a chloramphenicol-resistant gene (cat).

In still another aspect, the present invention provides a linear DNA fragment comprising: (a) a base sequence of a target gene; (b) a base sequence located at the 5'-terminus of the target gene, which has a forward ribosome recognition sequence of said recombinant vector and a homologous sequence to a portion of the region downstream of the promoter; and (c) a base sequence located at the 3'-terminus of the target gene which has the backward ribosome recognition sequence of the first selection marker gene of said recombinant vector, start codon and a homologous sequence to 5'-terminus of the first selection marker gene.

In still another aspect, the present invention provides a microorganism for homologous recombination, transformed with said recombinant vector and a plasmid containing a homologous recombination-promoting gene.

In the inventive microorganism, the homologous recombination-promoting gene is preferably a Redα/β or RecE/T gene.

In yet still another aspect, the present invention the primer for homologous recombination, which is set forth in SEQ ID NO: 7 and contains a backward ribosome recognition sequence, a start codon and a sequence of the 5'-terminus of chloramphenicol-resistant gene (cat).

The above and other objects, features and embodiments of the present invention will be more clearly understood from the following detailed description and the accompanying claims.

BRIEF DESCRIPTION OF THE DRAWINGS

FIG. 2 shows the base sequence of a cat site in recombinant vector pRMT according to the present invention, the cat site having deletions of a homologous base sequence and a ribosome recognition site (RBS).

FIG. 3 is a schematic diagram showing *E. coli* JM109 (DE3) pRMT-pKD46, a microorganism for expression according to the present invention.

DETAILED DESCRIPTION OF THE INVENTION, AND PREFERRED EMBODIMENT

Figure 1:
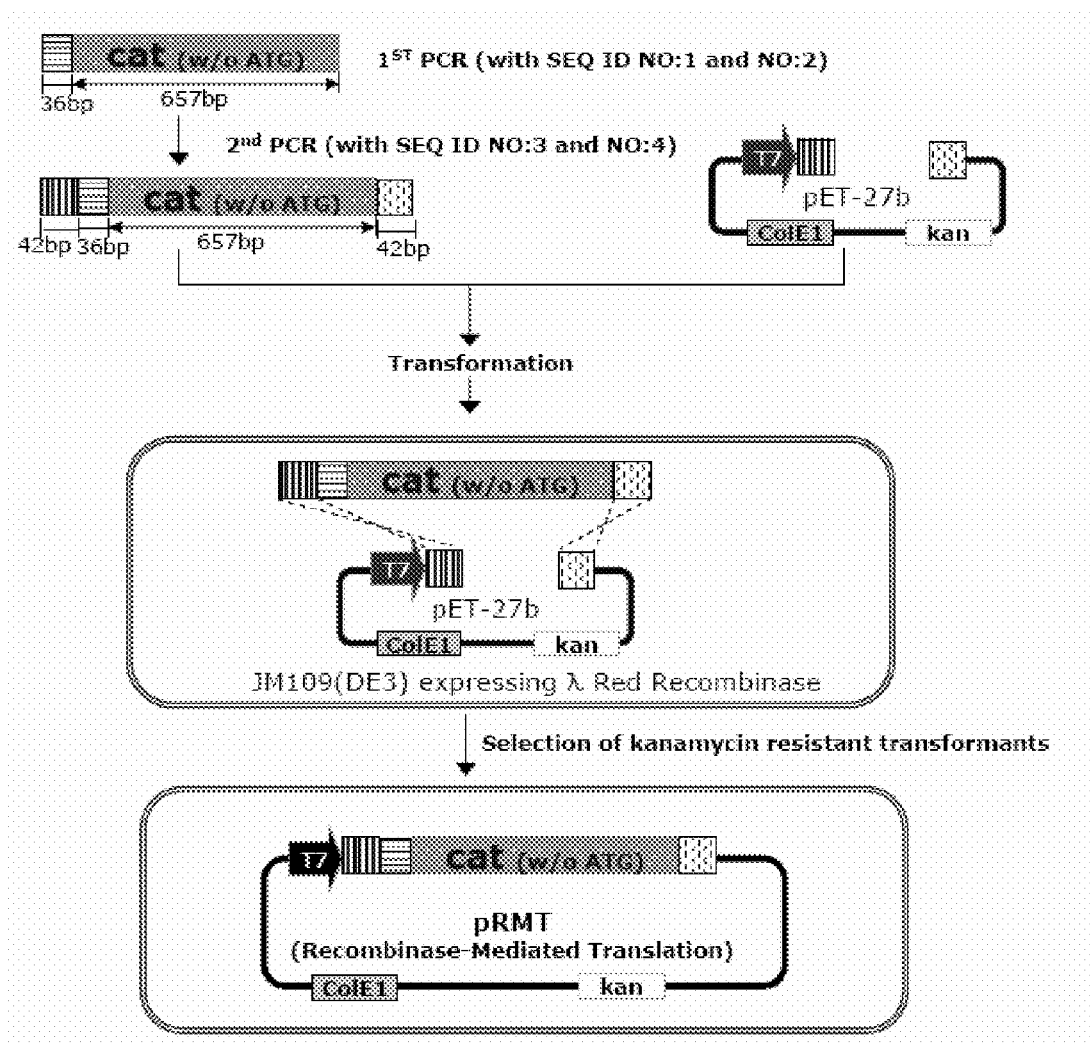
FIG. 1 shows a process for constructing recombinant vector pRMT according to the present invention.

The terms used herein are defined as follows: As used herein, the term "recombinant vector" refers to a recombinant plasmid allowing the expression of a target gene in a host cell by homologous recombination with the target gene.

As used herein, the term "ribosome recognition sequence" means a sequence containing a ribosome binding site (RBS).

As used herein, the term "forward ribosome recognition sequence" means a ribosome recognition sequence for expression of target gene is present in the recombinant vector and is to be located at the 5'-forward of the target gene, and the term "backward ribosome recognition sequence" means a ribosome recognition sequence which is located at the 3'-backward of the target gene and will function to restore the expression of the first selection mark gene in the recombinant vector, if the target gene is inserted into the recombinant vector.

As used herein, the term "selection marker gene" refers to a gene for selectively separating a transformed microorganism. As the selection marker gene, any gene can be used without limitations as long as it allows external confirmation of transformation. Examples of the selection marker gene, which can be used in the present invention, include various genes involved in the color development and antibiotic-resistant genes. Preferred gene is the antibiotic-resistant gene.

As used herein, the term "first selection marker gene" refers to a selection marker gene which is present in the recombinant vector and has no expression ability in itself, but is expressed by the recombination of a linear DNA containing the target gene, and the term "second selection marker gene" refers to a selection marker gene which is present in the recombinant vector and has expression ability in itself.

As used herein, the term "iTGR" (insert for Target Gene and Ribosome recognition sequence) fragment refers to a linear DNA fragment containing a ribosome recognition sequence and start codon for the expression of a target gene and a first selection marker gene.

As used herein, the term "plasmid" refers to a plasmid containing a gene for promoting homologous recombination. Examples of the gene for promoting homologous recombination include, but are not limited to, a red recombinase system or a RecA-encoding sequence.

As used herein, the term "forward homologous base sequence" means a base sequence homologous to the forward ribosome recognition sequence and a given length of the region downstream of the promoter of the recombinant vector, and the term "backward homologous base sequence" refers to a base sequence homologous to a given length of the 5'-terminus of the first selection mark gene. The term "given length" of the homologous base sequence refers to a length sufficient to cause homologous recombination and generally means a base sequence of 40-50 bases in length.

As used herein, the term "homologous recombination" means that a linear DNA fragment and a vectpr bind to each other by a homologous base sequence present in each of them, and other base sequences, which is not homologously recombinated, are synthesized, whereby a complete circular plasmid inserted with linear DNA is produced.

In the present invention, two homologous recombination processes sequentially occur as follows:
(1) A process of constructing a recombinant vector by inserting a first selection marker gene whose ribosome recognition sequence and start codon have been removed such that the selection marker gene has no expression ability, into a starting plasmid; and
(2) a process of recombineering a recombinant vector with a linear DNA fragment having: (i) a target gene; (ii) a base sequence located at the 5'-terminus of the target gene and homologous to the forward ribosome recognition sequence and a given length of the region downstream of the promoter of said recombinant vector prepared in the step (a); and (iii) a base sequence located at the 3'-terminus of the target gene and homologous to the backward ribosome recognition sequence and start codon of the first selection marker gene and a given length of the 5'-terminus of the first selection marker gene of the recombinant vector prepared in the step (a).

In the processes (1) and (2), a pair of respective base sequences (for 5'-terminus and 3'-terminus), must exist. As a result of the homologous recombination of the process (2), a recombinant vector containing 5'-(promoter→target gene→first selection marker gene)-3' is obtained.

Thus, the homologous base sequence at the 3'-terminus for inserting the target gene in the process (2) may be the same as the homologous base sequence at the 5'-terminus in the process (1), and it is preferable to use the same base sequences.

In the present invention, the primer for homologous recombination, which is used in the construction of the target gene-containing linear DNA, is a primer conferring the backward ribosome recognition sequence and start codon for expressing a chloramphenicol-resistant gene (cat) and the backward homologous base sequence homologous to a given length of the 5'-terminus of the cat gene on the 3'-terminus of the target gene.

The primer for homologous recombination may be used without any particular limitation regardless of the kind of the target gene in the inventive method for cloning and expressing the target gene by homologous recombination, as long as the first selection marker gene is the chloramphenicol-resistant gene (cat).

Hereinafter, each step of the inventive method for cloning and expressing the target gene by recombinase-mediated homologous recombination will be described in detail.

(1) Construction of Recombinant Vector and Microorganism for Homologous Recombination This step is a step of constructing a recombinant vector serving as an expression vector in cloning the target gene by homologous recombination according to the present invention. The recombinant vector comprises a first selection marker gene having deletions of a ribosome recognition sequence and start codon required for the expression of the first selection marker gene, and a second selection marker gene. In this step, a microorganism for homologous recombination, which comprises said recombinant vector and a plasmid containing a recombinase system is also constructed.

The 5'-terminus of the first selection marker gene is a base sequence for homologous recombination with a linear DNA fragment (iTGR) according to the present invention. Generally, to express a foreign (target) gene in a recombinant microorganism, a ribosome binding site (RBS) and start codon for synthesizing a polypeptide are required.

To construct the recombinant vector, any method can be used without limitations as long as it enables the first selection marker gene having deletions of the ribosome recognition sequence and start codon required for the expression of the first selection marker gene, and the second selection marker gene, to be included in the vector. However, in one embodiment of the present invention, the following can be used.

First, using an amplification method such as PCR, a first selection marker gene fragment, which has base sequences homologous to a parent vector at the 3'-terminus and 5'-terminus and is free of a start codon, is prepared. Also, the parent vector is cut with restriction enzymes to obtain a linearized parent vector that contains a promoter and a second selection marker gene.

The linearized first selection marker gene fragment and the linearized parent vector are transformed into a host cell containing a system for promoting homologous recombination, and a second selection marker is used to obtain a transformed cell containing a recombinant vector where the linearized first selection marker gene fragment is successfully homologously recombined with the parent vector.

According to said step, a host cell that contains the recombinant vector and a plasmid containing a system for promoting homologous recombination can be obtained.

In an embodiment of the present invention, a T7 promoter was used to construct plasmid pRMT including a cat gene having deletions of the ribosome recognition sequence and start codon required for the expression thereof (FIG. 1).

In the present invention, examples of the system for promoting homologous recombination include plasmids encoding a Redα/β or RecE/T system (e.g., plasmid pKD46 encoding a red-recombinase system). In an embodiment of the present invention, the red-recombinase system was used, but is not limited thereto.

The plasmid pKD46 comprises three genes, exo, bet and gam, which are essential for homologous recombination (FIG. 3). The exo gene encodes exonuclease that degrades double-stranded DNA in a 5'→3' direction to create a 3'-overhang. The bet gene encodes a protein that binds to single strand DNA exposed by the action of nuclease so as to promote the gene binding between complementary strands, and the gam gene encodes a protein that suppresses nuclease activity in microorganisms. The three genes are strictly regulated by an arabinose inducible promoter (Datsenko et al., *Proc. Natl. Acad. Sci.*, 12:6640, 2000).

Accordingly, in the inventive recombinant vector, if the recombination of the target gene with the homologous region occurs, the activation of the first selection marker gene and the expression of the target gene will simultaneously occur.

The method for cloning the target gene by homologous recombination using the inventive recombinant vector does not require a separate process, such as a process of linearizing a plasmid by treatment with restriction enzymes, because the recombinant vector can be stored and used in a state where it resides inside a host cell. Also, it is a vector system that can be selected and expressed at high speed when homologous recombination occurred in the vector.

(2) Preparation of DNA Fragment (iTGR) Containing Target Gene

This is a step of preparing a DNA fragment that contains a target gene and sequences essential for homologous recombination in order to clone the target gene by homologous recombination according to the present invention.

Figure 4:
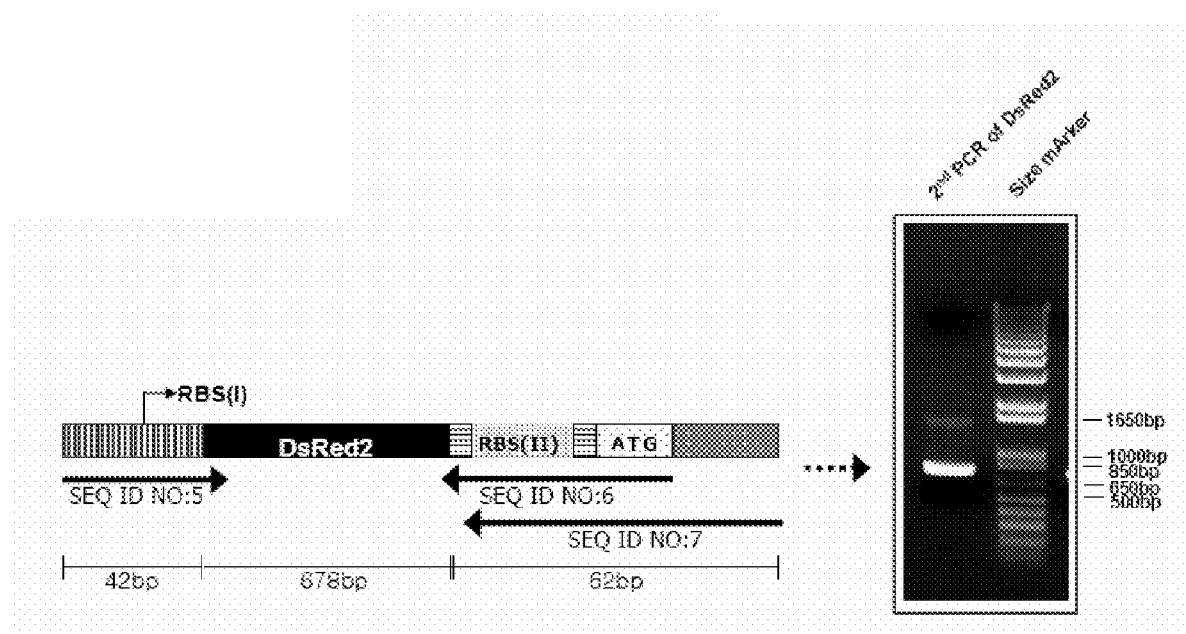
FIG. 4 is a schematic diagram of a DNA fragment (iTGR) containing a ribosome recognition sequence bound to target gene DsRed2 according to the present invention and is a photograph showing the electrophoresis of the DNA fragment.

Specifically, a forward homologous base sequence, which is homologous to a given length of the region downstream of the promoter of said recombinant vector, is linked to the 5'-terminus of the target gene, and a backward ribosome recognition sequence, a start codon and a backward homologous base sequence are linked to the 3'-terminus of the target gene, thereby preparing an iTGR (insert for Target Gene and RBS) fragment. To prepare the iTGR fragment, any method can be used without any particular limitation as long as it allows the preparation of the iTGR fragment having said structure. However, in one embodiment of the present invention, the following method can be used (FIG. 4).

First, the target gene is amplified using a first primer comprising the forward ribosome recognition sequence and a given length of the region downstream of the promoter of the recombinant vector, and a second primer comprising the start codon and backward ribosome recognition sequence of the first selection marker gene, thus obtaining a DNA fragment that comprises the target gene, a sequence in the downstream region of the promoter, and the start codon and backward ribosome recognition sequence of the first selection marker gene.

The DNA fragment is amplified by PCR using the first primer and a third primer comprising a sequence homologous to a portion of the 5'-sequence of the first selection marker gene, thus obtaining an iTGR fragment wherein a base sequence homologous to a given length of the region downstream of the forward homologous base sequence-promoter is linked to the 5'-terminus of the target gene, and the backward ribosome recognition sequence, the start codon and the backward homologous base sequence are linked to the 3'-terminus of the target gene.

As the target gene, any gene can be used as long as it can be expressed in a transformed microorganism. In Examples below, a gene encoding DsRed2, a kind of red fluorescent protein, was used as the target gene in order to allow the expression or non-expression of the target gene to be easily observed, but is not limited thereto.

(3) Recombination of Linear DNA (iTGR)

This is a step of transforming the target gene-containing linear DNA (iTGR) fragment prepared in the step (2) into the microorganism for homologous recombination obtained in the step (1), which contains the recombinant vector and the plasmid containing the system for promoting homologous recombination.

If the linear iTGR fragment according to the present invention is transformed into the microorganism for homologous recombination, the base sequence of the 5'-terminus of the linear iTGR fragment will complementarily bind to the base sequence of the 3'-terminus of the promoter of the recombinant vector due to homology between them, and the 3'-terminus of the linear iTGR fragment will complementarily bind to the 5'-terminus of the first selection marker gene due to homology between them.

If the homologous recombination is successfully made, the first selection marker gene will be converted into a state that can be expressed by the backward ribosome recognition sequence and start codon present in the linear DNA, and the inserted target gene can be expressed by the promoter present in the recombinant vector.

That is to say, if the homologous recombination according to the present invention occurs, it will be possible to simultaneously achieve the activation of the first selection marker gene and the expression of the target gene.

(4) Selection of Transformed Microorganism and Expression of Target Gene

This is a step of selecting a transformed microorganism where the homologous recombination between the target gene and the recombinant vector successfully occurred.

As described above, if the linear DNA according to the present invention is successfully homologously recombined with the recombinant vector, the expression of the first selection marker gene will be possible. Thus, in a condition where the first selection marker gene is expressed (e.g., antibiotic-containing medium, if the first selection marker gene is an antibiotic-resistant gene) or where the expression of the gene can be confirmed (e.g., a condition causing fluorescent development, if the first selection marker gene is a fluorescent gene), it is possible to select a microorganism having a successfully recombined target gene expressed therein. If necessary, in order to increase the efficiency of selection, it is also possible to select a microorganism transformed with the target gene in a condition where the simultaneous expression of the first selection marker (e.g., chloramphenicol) and the second selection marker gene (e.g., kanamycin) can be confirmed.

Separately from the confirmation of the expression of the selection marker gene, whether the target gene is expressed in the final, transformed microorganism can be measured using various methods depending on the physiological and chemical properties of the target gene.

Figure 7:
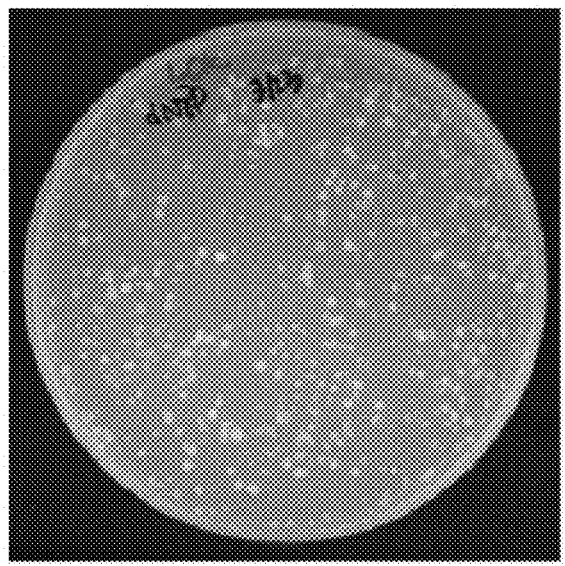
FIG. 7 is a photograph showing the expression of a red fluorescent gene in recombinant *E. coli* pRMT-pKD46 transformed with the target gene DsRed2 according to the present invention.

In Example below, in order to examine expression or non-expression in a simple and easy manner, a test was carried out using a red fluorescent protein gene as a target gene. The microorganism was transformed with the linear DNA containing the amplified red fluorescent protein gene and then selected using chloramphenicol resistance as the first selection marker. A colony having red fluorescence could be confirmed by irradiation to the selected colony with UV (FIG. 7).

It will be obvious to those skilled in the art that the recombinant vector according to the present invention can be constructed from various commercial or general starting materials according to a generally known method on the basis of the technical concept and idea of the present invention.

For example, pRMT according to Example of the present invention can be constructed from a commercially available vector according to a conventional in vivo cloning method as can be seen in Example below, and thus does not necessarily need to be deposited with the International Depositary Authority. For this reason, the deposition thereof was omitted.

EXAMPLES

Hereinafter, the present invention will be described in detail with reference to examples. It is to be understood, however, that these examples are for illustrative purposes only and are not to be construed to limit the scope of the present invention.

In the following examples, although a red fluorescent protein gene whose expression can be easily confirmed was used as a target gene to complete the present invention, it will be obvious to those skilled in the art that, even when any gene which can be expressed in a host cell upon transformation is used, results similar to those of the following examples can be obtained. Also, those skilled in the art will appreciate that a PCR product can be obtained from any gene using primers designed according to the method provided in the present invention, and can be used for the rapid cloning of mass amount of genes and a simple method of protein expression by transforming it into host cells containing recombinase and an expression vector.

Example 1

Preparation of Transformed Cells Containing Expression Vectors pRMT, and pRMT & pKD46

To construct recombinant vector pRMT comprising a chloramphenicol-resistant gene (cat) having deletions of a ribosome recognition sequence and start codon required for the expression thereof as a first selection marker gene, and a kanamycin-resistant gene (kan) as a second selection marker gene, a homologous recombination technique was used, wherein a DNA fragment containing a PCR-amplified cat gene having deletion of a start codon was linked to a plasmid vector linearized with restriction enzymes (FIG. 1).

Specifically, in the homologous recombination technique, the linear vector and the linear DNA fragment containing sites homologous to each other, were introduced into recombinant *E. coli* (arabinose-induced pKD46/*E. coli* JM109 (DE3)) by electroporation to clone. This method has advantages over a conventional restriction enzyme-ligase technique, in that it has no restriction in selecting DNA sequences.

To amplify a structural gene of cat having no start codon, PCR was performed using cat gene sequence-containing plasmid pSTV28 (Takara Co., Japan) as a template with the following primers of SEQ ID NOs: 1 and 2:

SEQ ID NO: 1: 5'-CCATCTTAGTATATTAGTTAAGTATAAGATATA
CATGAGAAAAAAATCACTGG-3'

SEQ ID NO: 2: 5'-TTACGCCCCGCCCTGCCACTCATCGC-3'

Wherein, bold characters represent 5' and 3' terminus of open reading frame of cat.

The primer of SEQ ID NO: 1 was constructed in a form having no start codon of cat in order to amplify inactive cat.

In order to insert the PCR-amplified cat gene fragment having no start codon into linearized parent vector pET27b (Novagen Co., USA) by homologous recombination, the cat gene fragment was subjected to PCR using the following primers of SEQ ID NOs: 3 and 4 containing a base sequence homologous to pET27b, thus obtaining a DNA fragment containing the cat gene and the base sequence homologous to pET27b.

SEQ ID NO: 3: 5'-<u>TCTAGAAATAATTTTGTTTAACTTTAAGAAGGA
GATATACAT</u>CCATCTTAGTATATTAGTTAAG-3'

SEQ ID NO: 4: 5'-GTGGTGGTGGTGGTGGTGCTCGACATCCTCGGG
GTCTTCCGGTTATTACGCCCCGCCCTGCCACTCATCGC-3'

Wherein, underlined region represents forward homologous region and bold characters represent 3' terminal of open reading frame of cat.

The parent vector pET-27b was cut with restriction enzyme BamHI and dephosphorylated by treatment with alkaline phosphotase.

Meanwhile, in order to prepare cells for transformation, *E. coli* JM109 (DE3) (Promega Co, USA) containing bacterial red-recombinase system-encoding plasmid pKD46 (*Proc. Natl. Acad. Sci. USA.*, 97:6640, 2000) was cultured in a medium containing 50 mM arabinose at 30° C. to an OD of 0.5, thus preparing electro-competent cells.

The plasmid pKD46 (FIG. 3) encoding the red-recombinase systems exo, bet and gam contains a temperature-sensitive replication origin, and the systems exo, bet and gam are strictly regulated under an arabinose-inducible promoter (Datsenko et al., *Proc. Natl. Acad. Sci.*, 12:6640, 2000).

The electro-competent cells thus prepared were transformed with 200 ng of the above-prepared PCR product containing the cat gene and the base sequence homologous to pET27b and with 10 ng of linearized pET-27b by electroporation, and then cultured overnight to induce homologous recombination. Then, the cultured strain was spread on LB (Luria-Bertani medium) agar medium containing kanamycin.

The linearized pET-27b cannot form circular DNA by itself. Thus, only if the PCR product and the linearized pET-27b are homologously recombined with each other in a suitable manner, a complete circular plasmid can be formed and a kanamycin-resistant gene can be expressed. Thus, the transformed cells can be selected because they can survive in the presence of kanamycin.

The selected colonies were subjected to colony PCR using a T7 promoter primer and a T7 terminator primer which are the base sequences of the pET-27b vector, thereby primarily confirming clones. Also, the selected colony was sequenced by DNA sequencing and named "recombinant vector pRMT" (Recombinase-Mediated Translation) (FIG. 2).

Recombinant *E. coli* containing both the selected transformant pRMT and the pKD46 was named "pRMT-pKD46" (FIG. 3). The recombinant *E. coli* was cultured in a medium containing 50 mM arabinose at 30° C. to an OD of 0.5, thus inducing the activation of red-recombinase. After completion of the induction of activation, the cultured cells were washed two times with cold sterile water and concentrated to an OD of 100.

The vector pRMT resides in the recombinant *E. coli* and does not require a separate preparation process, such as linearization of a plasmid by treatment with restriction enzymes, while it can be screened and expressed at high speed by antibiotic marking, if a homologous recombination reaction occurs in the vector.

Example 2

Processing of Target Gene

As a target gene for application to the recombinant vector pRMT constructed in Example 1, a red fluorescent protein gene (DsRed2) was used. The DsRed2 gene can be visually observed for the expression of protein by UV irradiation.

The red fluorescent protein gene (DsRed2) was amplified by PCR in the following manner. The red fluorescent protein gene (DsRed2) was amplified using a pDsRed2 (Clontech, USA) vector as a template with the following primers of SEQ ID NOs: 5 and 6.

```
SEQ ID NO: 5: 5'-TCTAGAAATAATTTTGTTTAACTTTAAGAAGGA
GATATACATATGGCCTCCTCCGAGAACG-3'

SEQ ID NO: 6: 5'-CTCCATATGTATATCTCCTTCTTATCTACAGGA
ACAGGTGGTGGCG-3'
```

Wherein, underlined region represents forward homologous region and italic characters represent antisense sequence of start codon and forward ribosome binding site, respectively.

The primer of SEQ ID NO: 5 contains a base sequence homologous to a given length of the region downstream of the T7 promoter of pRMT, and the primer of SEQ ID NO: 6 contains a start codon and backward ribosome recognition sequence for expressing cat as the selection marker of pRMT.

To extend the homologous base sequence, the above-obtained PCR product as a template was subjected to PCR using the primer of SEQ ID NO: 5 and the following primer of SEQ ID NO: 7.

```
SEQ ID NO: 7: GGGATATATCAACGGTGGTATATCCAGTGATTTTTT
TCTC CATATGTATA TCTCC TTC
``` wherein, the portion "bold alphabets+CAT (=ATG)" of the above SEQ ID NO: 7 represents the 5'-terminus of the cat gene. Underlined region represents backward homologous region and italic characters represent antisense sequence of start codon and backward ribosome binding site, respectively.

Herein, a sequence which is annealed to the target gene DsRed2 is present only in SEQ ID NO: 5 and SEQ ID NO: 6 and is not present in SEQ ID NO: 7, and the forward homologous and backward homologous base sequences binding to pRMT is included in SEQ ID NOs: 5 and 7 (underlined portions). Thus, because the primer of SEQ ID NO: 7 does not contain a portion which is annealed to the target gene, even if any target gene is used in a homologous recombination system utilizing the cat gene as the first selection marker gene, it can be used for PCR reaction. That is, with only two synthesized primers, it is sufficient for the PCR amplification of each of target genes.

The PCR reaction resulted in a linear DNA (iTGR) fragment wherein the forward homologous base sequence homologous to the promoter of pRMT was linked to the 5'-forward of the red fluorescent protein gene DsRed2, and the backward ribosome base sequence and start codon of the cat gene and the backward homologous base sequence were linked to the 3'-backward (FIG. 4).

Example 3

Transformation Using Electroporation

Figure 5:
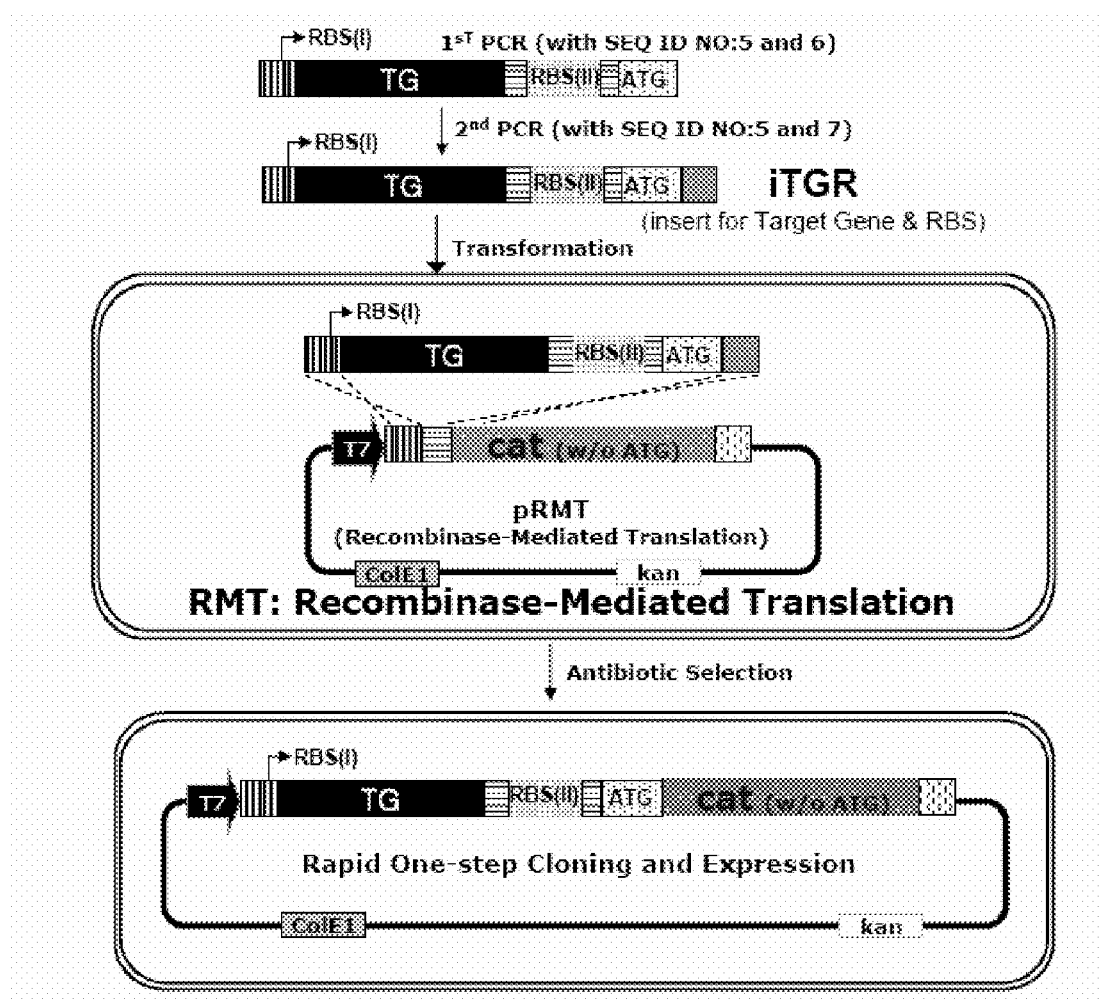
FIG. 5 shows a process wherein the DNA fragment containing the target protein according to the present invention is homologously recombined with recombinant vector pRMT.

The electro-competent cells containing pRMT & pKD46, prepared in Example 1, were transformed with 100 ng iTGR (a linear DNA fragment containing a DsRed2 gene) prepared in Example 2 by electroporation and then left to stand overnight at room temperature to induce homologous recombination. Because a chloramphenicol-resistant gene as the first selection marker gene is expressed in transformed cells where pRMT and iTGR were successfully homologously recombined with each other, the cells were spread on LB agar medium containing chloramphenicol so as to select colonies (FIG. 5).

Example 4

Analysis of Clones In Vivo Cloned

Figure 6:
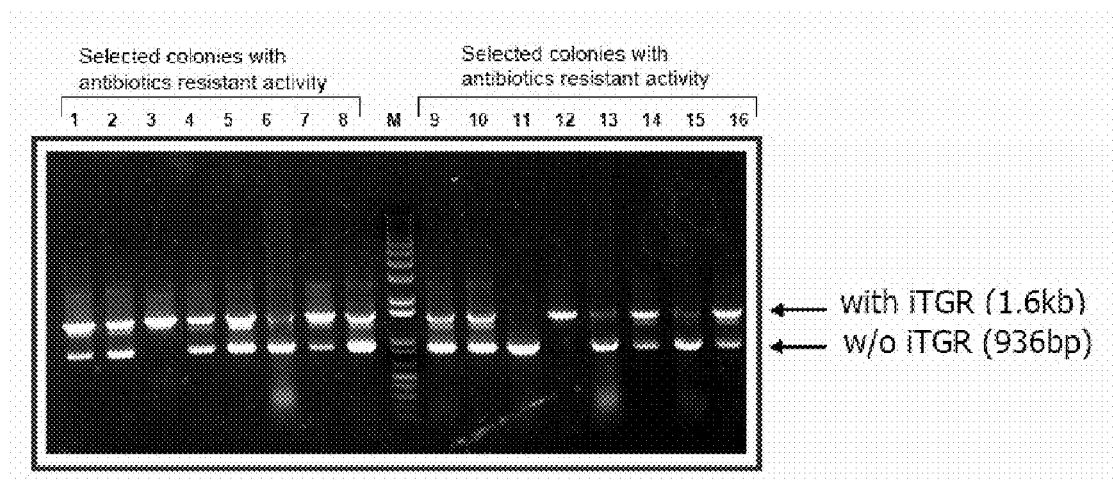
FIG. 6 is an electrophoresis photograph showing the result of the homologous recombination between the inventive recombinant vector pRMT and a DNA fragment (iTGR).

The transformed cells selected in Example 4 were subjected to colony PCR using a T7 promoter primer and a T7 terminator primer and electrophoresed (FIG. 6). Because, if the target gene DsRed2 is strongly expressed, the cells will have red fluorescence, whether the protein was expressed in the cells was examined by UV irradiation (FIG. 7).

In the colony PCR, the cloning of pRMT-iTGR was observed in all the colonies, and the PCR bands having various sizes were shown. This suggests that the level of in vivo cloning varies depending on cells.

Whether the target gene is cloned by homologous recombination can be confirmed using resistance to a first antibiotic, but in this case, a colony having the highest in vivo cloning level was difficult to be selected directly from the plate medium, due to poor quantitative characteristics. On the other hand, because the fluorescence of DsRed2 makes visual observation easy, it allowed quantitative analysis and selection of a colony having the highest expression rate (FIG. 7).

Meanwhile, because pRMT without bounding with iTGR does not give resistance to a first antibiotic, it could be easily eliminated even only by culturing the selected colonies in a small amount of liquid medium.

The expression of proteins can also be regulated even by the strength of a promoter or the copy number of plasmids. The replication origin of pRMT is derived from pBR322, and thus if the strong expression of the target gene is required, it can be achieved by replacing the replication origin with one derived from pUC. Similarly, if the weak expression of the target gene is required, it can be achieved by replacing the replication origin with one derived from p15A.

As described above, the present invention can provide the method for cloning and expressing a target protein by homologous recombination, which can easily clone the target gene and express a protein at high speed, without needing genetic engineering steps, such as digestion of a vector with restriction enzymes, and ligation of an inserted fragment. According to the present invention, because complicated genetic engineering steps, such as the restriction enzyme treatment and ligation of a vector and a target gene, are not required, the cloning of a gene can be performed without needing a high degree of skill, and enzyme cost can be reduced. Thus, the inventive method can be effectively used for the massive, high-speed cloning and protein expression of genes, and the pRMT-iTGR system according to the present invention can be used as an analysis means for improving high-efficiency recombinase.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for cloning and expressing a target gene by homologous recombination, the method comprising the steps of:

(a) performing homologous recombination with a recombinant vector and a linear insert for Target Gene and RBS (iTGR) DNA fragment, wherein the recombinant vector comprises:

(i) a promoter, (ii) an upstream ribosome recognition sequence of the vector, (iii) a first selection marker gene having deletions of its ribosome recognition sequence (downstream Ribosome Binding Site) and its start codon, and thus having no expression ability, and (iv) a second selection marker gene that can be expressed, and wherein the linear iTGR DNA fragment comprises:

(i) a base sequence of a target gene, (ii) a homologous sequence to a region downstream of the promoter and to the upstream ribosome recognition sequence in said vector, which are located before the base sequence of the target gene, and (iii) a downstream ribosome recognition sequence of the first selection marker gene, a translational start codon, and a homologous sequence to 5'-terminus sequence of the first selection marker gene, which are located behind the base sequence of target gene, and the linear iTGR DNA fragment can be inserted between the upstream ribosome recognition sequence in the vector and the first selection marker gene by the homologous recombination to express the target gene and the first selection marker gene, and (b) expressing the target gene by selecting a microorganism expressing the first selection marker gene and the second selection marker gene as a transformed microorganism introduced with the target gene.

2. The method for cloning and expressing a target gene by homologous recombination according to claim 1, wherein the promoter is T7 promoter, and the first selection marker gene is a chloramphenicol-resistant gene (cat).

3. The method for cloning and expressing a target gene by homologous recombination according to claim 1, wherein the microorganism further contains Redα/[3 or RecE/T gene.

4. The method for cloning and expressing a target gene by homologous recombination according to claim 1, wherein the recombinant vector is pRMT vector comprising SEQ ID NO: 8, and the linear iTGR DNA fragment comprises SEQ ID NO: 5, the target gene, and a sequence complementary to SEQ ID NO: 7.

* * * * *

UNITED STATES PATENT AND TRADEMARK OFFICE
CERTIFICATE OF CORRECTION

| | | |
|---|---|---|
| PATENT NO. | : 8,101,355 B2 | Page 1 of 1 |
| APPLICATION NO. | : 12/559345 | |
| DATED | : January 24, 2012 | |
| INVENTOR(S) | : Seung-Goo Lee et al. | |

It is certified that error appears in the above-identified patent and that said Letters Patent is hereby corrected as shown below:

Column 18, line 7: "Reda/[3" should be -- Red$\alpha/\beta$ --.

Signed and Sealed this
First Day of May, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 50
<212> TYPE: DNA
<213> ORGANISM: Artificial
<220> FEATURE:
<223> OTHER INFORMATION: primer

<400> SEQUENCE: 1
ccatcttagt atattagtta agtataagat atacatgaga aaaaaatcac          50

<210> SEQ ID NO 2
<211> LENGTH: 26
<212> TYPE: DNA
<213> ORGANISM: Artificial
<220> FEATURE:
<223> OTHER INFORMATION: primer

<400> SEQUENCE: 2
ttacgccccg ccctgccact catcgc                                    26

<210> SEQ ID NO 3
<211> LENGTH: 64
<212> TYPE: DNA
<213> ORGANISM: Artificial
<220> FEATURE:
<223> OTHER INFORMATION: primer

<400> SEQUENCE: 3
tctagaaata attttgttta actttaagaa ggagatatac atccatctta gtatattagt   60
taag                                                            64

<210> SEQ ID NO 4
<211> LENGTH: 71
<212> TYPE: DNA
<213> ORGANISM: Artificial
<220> FEATURE:
<223> OTHER INFORMATION: primer

<400> SEQUENCE: 4
gtggtggtgg tggtggtgct cgacatcctc ggggtcttcc ggttattacg ccccgccctg   60
ccactcatcg c                                                    71

<210> SEQ ID NO 5
<211> LENGTH: 61
<212> TYPE: DNA
<213> ORGANISM: Artificial
<220> FEATURE:
<223> OTHER INFORMATION: primer

<400> SEQUENCE: 5
tctagaaata attttgttta actttaagaa ggagatatac atatggcctc ctccgagaac   60
g                                                               61
```

-continued

```
<210> SEQ ID NO 6
<211> LENGTH: 46
<212> TYPE: DNA
<213> ORGANISM: Artificial
<220> FEATURE:
<223> OTHER INFORMATION: primer

<400> SEQUENCE: 6
ctccatatgt atatctcctt cttatctaca ggaacaggtg gtggcg            46

<210> SEQ ID NO 7
<211> LENGTH: 58
<212> TYPE: DNA
<213> ORGANISM: Artificial
<220> FEATURE:
<223> OTHER INFORMATION: primer

<400> SEQUENCE: 7
gggatatatc aacggtggta tatccagtga ttttttctc catatgtata tctccttc  58

<210> SEQ ID NO 8
<211> LENGTH: 785
<212> TYPE: DNA
<213> ORGANISM: Artificial
<220> FEATURE:
<223> OTHER INFORMATION: pRMT vector

<400> SEQUENCE: 8
taatacgact cactataggg gaattgtgag cggataacaa ttcccctcta gaaataattt   60
tgtttaactt taagaaggag atatacatcc atccatctta gtatattagt taagtataag  120
atatacatga gaaaaaaatc actggatata ccaccgttga tatatcccaa tggcatcgta  180
aagaacattt tgaggcattt cagtcagttg ctcaatgtac ctataaccag accgttcagc  240
tggatattac ggcctttta aagaccgtaa agaaaaataa gcacaagttt tatccggcct  300
ttattcacat tcttgcccgc ctgatgaatg ctcatccgga attccgtatg gcaatgaaag  360
acggtgagct ggtgatatgg gatagtgttc acccttgtta caccgttttc catgagcaaa  420
ctgaaacgtt ttcatcgctc tggagtgaat accacgacga tttccggcag tttctacaca  480
tatattcgca agatgtggcg tgttacggtg aaaacctggc ctatttccct aaagggttta  540
ttgagaatat gttttttcgtc tcagccaatc cctgggtgag tttcaccagt tttgatttaa  600
acgtggccaa tatggacaac ttcttcgccc ccgttttcac catgggcaaa tattatacgc  660
aaggcgacaa ggtgctgatg ccgctggcga ttcaggttca tcatgccgtt tgtgatggct  720
tccatgtcgg cagaatgctt aatgaattac aacagtactg cgatgagtgg cagggcgggg  780
cgtaa                                                               785
```